(12) United States Patent
Nakayama et al.

(10) Patent No.: US 9,408,601 B2
(45) Date of Patent: Aug. 9, 2016

(54) MANUFACTURING METHOD OF AN EYELESS SUTURE NEEDLE

(75) Inventors: Yokichi Nakayama, Sagamihara (JP); Shinichiro Nakayama, Sagamihara (JP)

(73) Assignee: KABUSHIKI KAISHA IKEN KOUGYO, Sagamihara-Shi (JP)

( * ) Notice: Subject to any disclaimer, the term of this patent is extended or adjusted under 35 U.S.C. 154(b) by 36 days.

(21) Appl. No.: 14/236,682

(22) PCT Filed: Aug. 2, 2012

(86) PCT No.: PCT/JP2012/069705
§ 371 (c)(1),
(2), (4) Date: Feb. 3, 2014

(87) PCT Pub. No.: WO2013/021911
PCT Pub. Date: Feb. 14, 2013

(65) Prior Publication Data
US 2014/0166225 A1 Jun. 19, 2014

(30) Foreign Application Priority Data
Aug. 5, 2011 (JP) .................. 2011-172275

(51) Int. Cl.
| | |
|---|---|
| *A61B 17/06* | (2006.01) |
| *B21G 1/08* | (2006.01) |
| *B24B 19/16* | (2006.01) |
| *B21J 5/02* | (2006.01) |
| *B21G 5/02* | (2006.01) |
| *A61B 17/00* | (2006.01) |

(52) U.S. Cl.
CPC ............ *A61B 17/06066* (2013.01); *B21G 1/08* (2013.01); *B21J 5/027* (2013.01); *B24B 19/16* (2013.01); *A61B 2017/00526* (2013.01); *A61B 2017/06028* (2013.01)

(58) Field of Classification Search
CPC ............ B21G 1/08; B24B 19/16; B21C 1/16; B21C 1/22; B21C 1/24; B21C 5/003; A61B 17/06066; A61B 2017/00526; A61B 2017/06028; B21J 5/027
USPC ............ 72/283, 367.1, 368, 370.25, 112, 115
See application file for complete search history.

(56) References Cited

U.S. PATENT DOCUMENTS

| | | | | |
|---|---|---|---|---|
| 2,208,606 | A | * | 7/1940 | Smith .............................. 72/348 |
| 2,296,743 | A | * | 9/1942 | Common ...................... 228/144 |

(Continued)

FOREIGN PATENT DOCUMENTS

| | | |
|---|---|---|
| EP | 0 296 776 | 12/1988 |
| EP | 1 323 483 | 7/2003 |

(Continued)

OTHER PUBLICATIONS

European Search Report dated Dec. 12, 2014, Application No. 12822394.8, 7 pages.

*Primary Examiner* — David Bryant
*Assistant Examiner* — Lawrence Averick
(74) *Attorney, Agent, or Firm* — Rankin, Hill & Clark LLP (57) ABSTRACT

A pipe element tube 23 is manufactured by a manufacturing method including step S1-1 for obtaining the pipe element tube 23 by rolling a stainless steel plate material 21 and welding an abutting portion, a core drawing step S1-2 for reducing a diameter and adjusting a thickness of the pipe element tube 23 by using a cored bar 24, and a tube drawing step S1-3 for reducing the diameter and adjusting an outer form of the pipe element tube 23 without using a cored bar. By adjusting repetition times of the core drawing step S1-2 and the tube drawing step S1-3, a uniform concavity and convexity are provided on an inner circumferential surface of the pipe element tube 23. Then a pipe 12 having an annular shaped cross section obtained by cutting the pipe element tube 23 and a linear material 11 having a circular cross section are joined (S2).

3 Claims, 5 Drawing Sheets

(56) References Cited

U.S. PATENT DOCUMENTS

| | | | | |
|---|---|---|---|---|
| 2,620,028 | A | * | 12/1952 | Kohut ................... 163/5 |
| 3,540,112 | A | * | 11/1970 | Knox .................... 29/414 |
| 3,794,803 | A | * | 2/1974 | Valdeck ................. 219/61 |
| 3,835,912 | A | * | 9/1974 | Kristensen ....... A61B 17/06004 163/5 |
| 4,541,470 | A | * | 9/1985 | Pavel ................ B21G 1/04 163/5 |
| 6,877,652 | B2 | * | 4/2005 | Ooyauchi et al. ......... 228/170 |
| 2010/0036415 | A1 | * | 2/2010 | Cabezas ................. 606/223 |

FOREIGN PATENT DOCUMENTS

| | | |
|---|---|---|
| JP | 63-183048 | 7/1988 |
| JP | 63-317146 | 12/1988 |
| JP | 63-317148 | 12/1988 |
| JP | 01-162590 | 6/1989 |
| JP | 02-011239 | 1/1990 |
| JP | 02-051516 | 4/1990 |
| JP | 2003-024334 | 1/2003 |
| JP | 2004-222899 | 8/2004 |
| JP | 2005-052654 | 3/2005 |
| JP | 2010-51623 | 3/2010 |

* cited by examiner

MANUFACTURING METHOD OF AN EYELESS SUTURE NEEDLE

TECHNICAL FIELD

The present invention relates to a manufacturing method of an eyeless suture needle.

In a surgical operation and the like, an eyeless suture needle in which a suture thread is caulked and fixed to a blind hole of a thread attaching portion is used. Conventionally, first a needle tip portion and a needle body portion are processed to a round rod material, and then an opposite side of the needle tip portion is cut to a predetermined length. Thereafter, the blind hole of the thread attaching portion is formed by opening a hole to the cut surface to be parallel to a needle axis by a drill, laser, or electric discharge machining or the like (refer to Patent Literatures 1 to 3). Moreover, in a case of manufacturing a relatively long eyeless suture needle, there were cases where the needle tip portion and the needle body portion was processed by cutting to a predetermined length after providing the blind hole.

There has been also proposed to process the needle tip portion and the needle body portion to the round rod material and thereafter provide the blind hole by laser welding a pipe to a needle base, and further thereafter to conduct a bending process of the needle body portion (refer to Patent Literatures 4 to 6). However, it is very difficult to laser weld the pipe to a very thin needle body portion, and therefore it has not been practically used.

A general depth of the blind hole is approximately 2.5 times the blind hole diameter in view of the processing difficulty. For example, in a case of an eyeless suture needle of needle total length 15 mm, needle diameter 0.5 mm, blind hole diameter 0.25 mm, the depth of the blind hole is approximately 0.7 mm. The suture thread is caulked in a state where the suture thread is inserted to such shallow blind hole, and fixed to the blind hole.

In the Pharmaceutical Affairs Law, it is set forth that the drawing strength when separating the suture needle and the suture thread needs to be equal to or more than half of the suture thread strength. However, it is difficult to obtain such drawing strength.

If the caulking pressure is weakened, the tread will be cast-off by a small drawing force. On the other hand, if the caulking pressure is strengthened, problems occur such as the breakage of the suture needle or the like. Even by carefully adjusting the caulking pressure, it is very difficult to completely dissolve the defect of the drawing strength. Furthermore, a needle separated from the suture thread by a drawing strength test cannot be reused, and this becomes a cause of high cost.

In order to improve this problem, various conceptions has been proposed to increase the fixing strength of the suture thread by providing concavity and convexity or the like to an inner surface of the blind hole. For example, Patent Literature 1 discloses to form a twill line knurl in the inner surface of the blind hole. In Patent Literature 2, it is disclosed to open a prepared hole by laser processing or the like, and to provide additional processing by a drill or a tungsten round rod to expand the diameter of the hole, and also to leave a part of the prepared hole remained and form concavity and convexity. Moreover, Patent Literature 3 discloses to chamfer and to provide concavity and convexity to the inner surface of the hole by shot blasting.

CITATION LIST

Patent Literature

Patent Literature 1: Japanese Utility Model Application Laid-Open No. H02-51516
Patent Literature 2: Japanese Patent Application Laid-Open No. H02-11239
Patent Literature 3: Japanese Patent Application No. 2003-24334
Patent Literature 4: Japanese Patent Application Laid-Open No. S63-317148
Patent Literature 5: Japanese Patent Application Laid-Open No. H01-162590
Patent Literature 6: Japanese Patent Application Laid-Open No. 2005-52654

SUMMARY OF INVENTION

Technical Problem

However, as recited in Patent Literature 1, when the twill line knurl is formed by cutting, a sharp convex portion is formed. Therefore, especially in a case of attaching a braided suture thread to the blind hole, the outer thread around the core thread is damaged at the convex portion and becomes the cause of breakage. Moreover, in a case where the hole diameter of the blind hole is equal to or less than 0.3 mm, processing is very difficult.

Moreover, as recited in Patent Literature 2, in a case of providing the blind hole by expanding the diameter of the prepared hole opened by laser processing, the concavity and convexity of the inner surface of the blind hole are not uniform. Moreover, since only large concavity and convexity are generated on the inner surface of the prepared hole formed by laser processing or the like, the fixation effect is poor.

It is disclosed in Patent Literature 2 that if additional processing is provided using a drill with respect to the prepared hole formed by laser processing, a spiral-like concavity and convexity is formed, and the fixation effect is increased. However, in a case of difficult-to-cut materials such as stainless steel material, by a slight abrasion of an outer periphery cutting blade portion of the drill tip end, a reamer like effect is generated and cuts to form a mirror surface. Therefore, the fixation effect is not so high. These also apply to a case the blind hole is formed only by a drill, and becomes the cause of insufficient drawing strength of the suture thread.

Moreover, as is recited in Patent Literature 3, even by shot blasting, the concavity and convexity of the inner surface of the blind hole is limited to the entrance portion of the hole. Therefore, the fixation effect is poor. Moreover, it is not preferable since the outer diameter portion is chamfered larger than the entrance portion of the hole.

In view of the above, it is an object of the present invention to provide a manufacturing method of an eyeless suture needle capable of making the drawing strength of the suture thread large and uniform.

Solution to Problem

A manufacturing method of an eyeless suture needle of the present invention comprises a step of obtaining a pipe-like material by rolling a metal plate material, and welding abutting portions, a step of manufacturing a pipe-like member including a core drawing step of reducing a diameter and adjusting a thickness of the pipe-like material using a cored bar and a tube drawing step of reducing the diameter and adjusting an outer form of the pipe-like material without using the cored bar, and by adjusting a number of times of repetition of the core drawing step and the tube drawing step, forming the pipe-like member having an annular shape cross section and having uniform concavity and convexity formed on an inner circumferential surface thereof, and a step of, while abutting linear members each having an annular shape cross section to end faces of the pipe-like member, joining them by butt resistance welding, and forming a joining portion in flush to obtain a needle base material which becomes a base material of two eyeless suture needles, and thereafter cutting each of both end portions of the pipe-like member of the needle base material with a length for thread attaching portions being remained.

According to the manufacturing method of the eyeless suture needle of the present invention, by joining the pipe-like member with uniform concavity and convexity formed on an inner circumferential surface in advance, it is able to easily provide a thread attaching portion having a blind hole. Furthermore, it is able to lessen the shape error of the blind hole, to make the surface roughness of the inner surface of the blind hole uniform, and to make the depth of the blind hole sufficient. Therefore, it is able to increase and equalize the drawing strength of the suture thread which is caulked and fixed to the blind hole.

The concavity and convexity are formed on the inner circumferential surface of the pipe-like member by adjusting the number of times of repetition of the core drawing step and the tube drawing step. Therefore, it is able to easily provide uniform concavity and convexity on the inner circumferential surface of the pipe-like member. Moreover, since it is able to equalize the inner diameter, outer diameter, and the surface roughness by the concavity and convexity or the like of the pipe-like member, the shape of the blind hole becomes uniform.

Since the pipe-like member and the linear members having circular shape cross sections are joined by butt resistance welding, there is no need to rotate the pipe-like member and the linear members as in the case of joining by laser welding or the like. Therefore, stable joining is possible, and the processing speed is fast, and the facility is simplified.

By the way, conventionally, a pipe-like member having a same length as the thread attaching portion was joined to one end of the linear member to form the needle base material. In this regard, it was not possible to secure sufficient holding length when forming the joining portion in flush, and only long eyeless suture needles could be manufactured by such method of constituting the thread attaching portion by the pipe-like member.

In the manufacturing method of the eyeless suture needle of the present invention, two eyeless suture needles are obtained from the needle base material obtained by joining the linear members to each of the both ends of the pipe-like member.

Therefore, since the needle base material is a base material for two eyeless suture needle, it has a length more than two times the conventional needle base material. Therefore, the portion capable of holding in the step of forming the joining portion in flush becomes longer compared to before. More specifically, it is able to hold the pipe-like member or the linear member on the opposite side. Therefore, when forming the joining portion in flush, it is able to sufficiently secure holding length of the needle base material. Moreover, after obtaining the needle base material by forming the joining portion in flush, two eyeless suture needles can be manufactured by cutting each of the both end portions of the pipe-like member while leaving a necessary length as the thread attaching portion. Therefore, it is able to manufacture short eyeless suture needles which could not be manufactured by the conventional method of constituting the thread attaching portion by the pipe-like member.

Moreover, the production efficiency is superior since two eyeless suture needles can be manufactured from one needle base material. Since the needle base material is long, it becomes easier to process the linear member of the needle base material to form a needle tip portion and a needle body portion.

Furthermore, in the manufacturing method of the eyeless suture needle of the present invention, it is preferable that a surface roughness Rz of the inner circumferential surface of the pipe-like member is 5 µm to 15 µm.

In such case, it is sufficient to strongly caulk and fix the suture thread inserted into the blind hole, and there is less risk of damaging an outer thread such as a braided suture thread or the like.

Moreover, in the manufacturing method of the eyeless suture needle of the present invention, it is preferable to comprise a step of chamfer process of an opening portion of the pipe-like member in a plurality of chamfer angles using a plurality of drills having different point angles.

In such case, the sharpness of the edge of the chamfered portion is reduced compared to a case of providing chamfer process to the opening portion of the pipe-like member by a single chamfer tool, and also it is able to prevent the generation of burr, and restrain the suture thread from being torn off by the edge.

BRIEF DESCRIPTION OF THE DRAWINGS

FIG. 1A to FIG. 1C show an eyeless suture needle of an embodiment of the present invention, in which

DESCRIPTION OF EMBODIMENTS

Hereinafter, an eyeless suture needle and a manufacturing method thereof are explained with reference to the drawings. First, the cause of insufficient drawing strength of a suture thread caulked and fixed to a blind hole of a thread attaching portion of the eyeless suture needle will be considered.

[Cause of Insufficient Drawing Strength]

The direct cause of insufficient drawing strength of the suture thread is considered to be the defect of separation of the suture thread by dropping out from the blind hole or separation of the suture thread by being torn off. As a result of analysis by the inventor, it was found that these defects are related to hole diameter error of the blind hole, outer diameter error of the suture thread, surface roughness of an inner surface of the blind hole, shape of an opening portion of the blind hole, and a depth of the blind hole. Therefore, if each of these factors are made to be appropriate, it is able to largely decrease the possibility of occurrence of insufficient drawing strength. Hereinafter, each of these factors will be considered.

[Hole Diameter Error of the Blind Hole]

In conventional laser processed blind holes, it is known that the hole shape widely vary and the hole diameter error is large. In drill processed blind holes, a slight core warp of the tip end of the drill changes the hole diameter largely. Especially, thin drills with a drill diameter equal to or less than 0.5 mm have low stiffness. Therefore, accurate grinding by the drill tip end is difficult. Even if accurately ground, as a characteristic of drill process, when the distal end outer peripheral cutting blade is sharp, the hole diameter becomes larger than the drill diameter, while the hole diameter becomes smaller along with abrasion, and in due time, the friction resistance of the inner surface of the hole and the outer periphery of the drill increases, and the drill is broken and damaged. Even if re-polished before the drill is broken and damaged, it is not able to avoid the occurrence of large error of the hole diameter.

As explained above, conventional blind holes processed by laser or drill have large hole diameter error.

[Outer Diameter Error of the Suture Thread]

Since the suture thread itself has flexibility, it is difficult to equalize the outer diameter. Regarding blind suture thread, outer diameter error occurs due to outer diameter error of the original yarn used, way of tightening when braiding, concentration of the coating agent, and the like. Moreover, for monofilament suture thread such as nylon suture thread, outer diameter error of approximately 20 μm occurs due to the setting of various conditions at the time of spinning.

However, the outer diameter error of these suture threads are relatively small within the same production lot. Therefore, the error is to a degree which can be ignored if it is managed not to mix the production rod.

[Surface Roughness of the Inner Surface of the Blind Hole]

There are many cases that the drawing strength is insufficient due to the inner surface of the blind hole. Laser processed blind holes vary its hole shape itself due to minute laser focus difference, and also a mirror surface, wave-like irregularity, and oxidized metal adhesion, or the like is generated on its inner surface. Therefore, the surface roughness of the inner surface of laser processed blind hole does not become uniform.

The inner surface of a drill processed blind hole is usually smooth. Therefore, in order to strongly fix the suture thread, it is necessary to strengthen the caulking pressure. However, if the caulking pressure is strengthened, torn off is likely to happen by the edge of a chamfer processed portion of an opening portion of the blind hole.

Moreover, when ground by a drill immediately after polished, a spiral-shaped pattern is made on the inner surface of the blind hole by the drill tip outer peripheral cutting blade. In a case of difficult-to-cut materials such as stainless steel material, due to abrasion of a corner portion of the drill tip outer peripheral cutting blade, the inner surface of the hole becomes a mirror surface. As such, it is difficult to equalize the surface roughness of the inner surface of a drill processed blind hole.

[Shape of the Opening Portion of the Blind Hole]

The shape of the opening portion of the blind hole largely affects the torn off defect of the caulked and fixed suture thread. Generally, corner chamfering is provided to the opening portion considering the ease of inserting the suture thread. In such corner chamfering, a sharp edge is generated at both ends of the chamfered deleted portion. Even if the angle of the chamfer tool is changed, the sharp edge is drawn to either one of the both ends, and it is not possible to resolve harmful edges. Moreover, as the chamfer tool is worn, burr is generated at the edge, and the problem becomes worse.

If there is an edge in the opening portion, when the suture thread is inserted, and caulked and fixed to the blind hole, the sharpness of the edge inside negatively affects the suture thread to be torn off at the time of caulking, and the sharpness of the edge of the outer peripheral end portion negatively affects the suture thread to be torn off in a case where the suture thread is drawn in an orthogonal direction with respect to the suture needle.

It is able to solve these problems if the chamfer portion is made arc-like. However, it is very difficult to manufacture a chamfer tool having an arc-like shape corresponding to a widely used blind hole having a minute diameter of approximately 0.15 mm to 0.4 mm. Therefore, practically, the chamfer portion is not formed to have an arc-like shape.

[Depth of the Blind Hole]

To provide the blind hole with a sufficient and uniform depth is an important factor in order to strongly caulk and fix the suture thread. It was found that the drawing strength of the suture thread decreases by approximately 15% or more in a case where the depth of the blind hole is insufficient and the whole suture thread inside the hole is compressed by caulking compared to a case where the depth of the blind hole is sufficient and the inner end portion of the suture thread inside the hole is not compressed by caulking (refer to FIG. 5).

A laser processed blind hole has a narrow innermost portion and it is difficult to equalize the depth. Moreover, in a drill processed blind hole, in a case of a suture needle having a difficult-to-cut materials such as stainless steel material as its material, it is necessary to set the depth of the blind hole to minimum. However, even if the depth of the blind hole is set to be minimum, the frictional wear of the drill is extreme and the number of times of re-polishing the drill increases. Therefore, setting error of the drill is likely to occur.

Here, if the depth of the blind hole is made to be three times or more of the hole diameter, occurrence of defect at the time of caulking due to the depth error is improved. However, in this case, the process cost becomes very high due to process difficulty, increase of machining time, extreme frictional wear of the drill and the like.

As described above, there are many factors for the drawing strength of the suture thread being insufficient in the blind holes of the thread attaching portion of conventional eyeless suture needles. Especially, the unevenness of the drawing strength of the suture thread becomes a big problem for intermediate pressure caulked suture needles in which the drawing strength is adjusted so as to be used in a surgical form of separating the suture needle and the suture thread during the surgery.

It is an object of the present invention to provide a manufacturing method of an eyeless suture needle capable of solving various problems related to the blind hole of the thread attaching portion of the eyeless suture needle as mentioned above. The present invention especially aims to provide a manufacturing method of an eyeless suture needle capable of reducing the tear of suture thread, risk of thread cast-off, and unevenness of drawing strength, and also capable of increasing and equalizing the drawing strength of the suture thread.

In order to do so, as described above, it is necessary to reduce the inner diameter error of the blind hole, optimize and equalize the surface roughness of the inner surface of the blind hole, make the depth of the blind hole sufficient, and to make the shape of the opening portion of the blind hole to have a shape with less risk of damaging the thread.

[Eyeless Suture Needle]

Hereinafter, an embodiment of an eyeless suture needle of the present invention is explained with reference to the drawings.

Figure 1A:
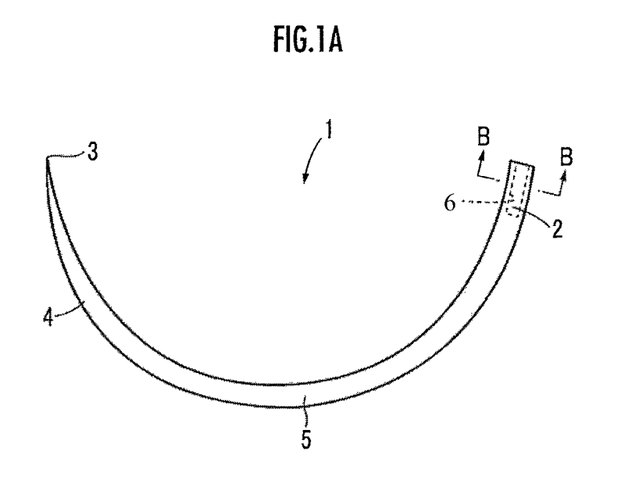
FIG. 1A shows an overall view.

As is shown in FIG. 1A, eyeless suture needle 1 is equipped with a thread attaching portion 2 to which a suture thread 41 (refer to FIG. 5) is caulked and fixed, a needle tip portion 4 having a needle tip 3 at the distal end, and an arc-shaped curved needle body portion 5 provided between the thread attaching portion 2 and the needle tip portion 4.

Figure 1B:
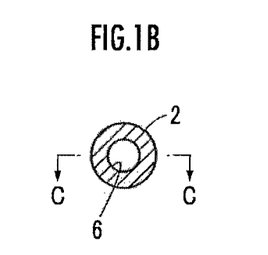
FIG. 1B shows a cross sectional view of line B-B of FIG. 1A.

The needle attaching portion 2 is formed with a blind hole 6 to which the suture thread 41 (refer to FIG. 5) inserted inside thereof is caulked and fixed, and the cross section thereof has an annular shape as shown in FIG. 1B. On an inner circumferential surface 6a of the blind hole 6, uniform satin-like shaped concavity and convexity are formed.

It is preferable that the surface roughness of the inner circumferential surface 6a of the blind hole 6 is sufficiently rough in order to strongly caulk and fix the suture thread 41, and also has a roughness of a degree which does not damage the outer thread such as the braided suture thread or the like. In order to do so, as a result of an experiment, it was found to be most suitable when the surface roughness (Rz value) of the inner circumferential surface was 5 μm to 15 μm. By doing so, the surface roughness of the inner surface of the blind hole becomes uniform and also it is able to equalize the drawing strength of the suture thread 41 caulked and fixed to the blind hole 6.

Figure 1C:
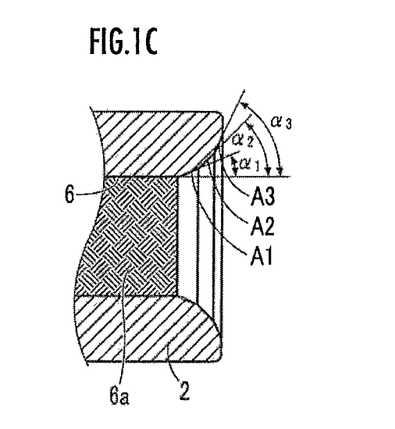
FIG. 1C shows a cross sectional view of line C-C of FIG. 1B.

Moreover, the opening portion of the blind hole 6 is chamfered in a plurality of chamfer angles. Here, as shown in FIG. 1C, the opening portion of the blind hole 6 is configured of a first surface A1 with a chamfer angle α1 of 22 degrees, a second surface A2 with a chamfer angle α2 of 46 degrees, and a third surface A3 with a chamfer angle α3 of 68 degrees. By doing so, compared to a case where the opening portion of the blind hole 6 is chamfer processed by a single chamfer angle, the sharpness of the edge of the chamfered portion is lessened and becomes substantially arc-like (substantially horn-like) shape, and enables to restrain the suture thread 41 from being torn off by the edge.

It is fine if the opening portion of the blind hole 6 is chamfered by a plurality of chamfer angles, and for example, it may be chamfered by two chamfer angles. In this case, for example, one of the chamfer angles may be 30 degrees and the other chamfer angle may be 60 degrees. Here, in order to prevent the generation of burr at the time of chamfer processing, it is preferable to have the tip angle of each edge of the chamfer portion to be 150 degrees or more.

[Manufacturing Method of the Eyeless Suture Needle]

Hereinafter, a manufacturing method of the eyeless suture needle of the embodiment of the present invention will be explained with reference to the drawings.

Figure 2:
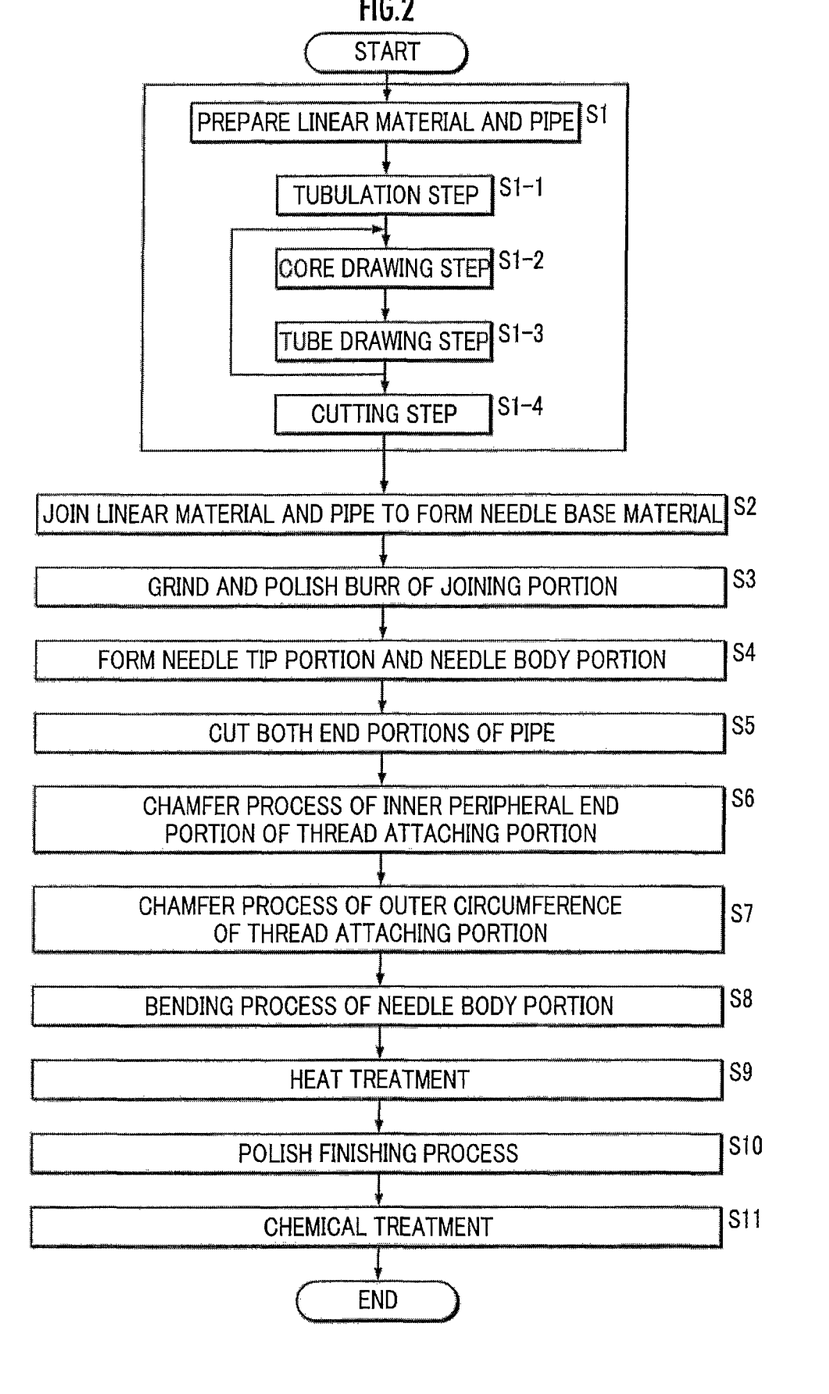
FIG. 2 is a process flow chart showing a manufacturing method of the eyeless suture needle.

As shown by S1 of FIG. 2, first, a step of preparing a linear material (round bar material) 11 which is a solid linear-like member of a predetermined length and a pipe (cylindrical material) 12 which is a pipe-like member of a predetermined length, is performed.

The linear material 11 and the pipe 12 are in this case both made of stainless steel, and their outer diameters are equal, preferably 0.3 mm to 1.3 mm. Moreover, it is preferable that a hole diameter of the pipe 12 is 40% to 70% of the outer diameter. It is preferable that the linear material 11 and the pipe 12 are formed of the same material, however, they may be of different materials taking account of the workability of the pipe 12. As the material of the linear material 11 and the pipe 12, for example, SUS304 can be used.

The linear material 11 and the pipe 12 are lengthy suitable for the steps explained later. It is preferable that the length of the linear material 11 is the same or a little longer than a central axis length of needle tip portion 4 and a needle body portion 5 of the completed product of the eyeless suture needle 1 (refer to FIG. 1A). The length of the pipe 12 is a length suitable for holding at each processing steps.

The outer circumferential surface of the pipe 12 is a mirror surface and an uniform satin-like concavity and convexity are formed on the inner circumferential surface of the pipe 12. As explained later, the pipe 12 becomes a thread attaching portion 2 (refer to FIG. 1A), and it is optimum when the surface roughness (Rz value) of its inner circumferential surface is 5 μm to 15 μm.

Such pipe 12 can be manufactured by a manufacturing method including tubulation step S1-1, core drawing step S1-2, and tube drawing (sinking) step S1-3, as explained below.

Figure 3A:
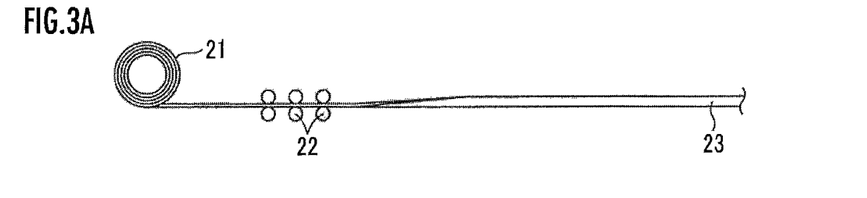
FIG. 3A to FIG. 3H are schematic views showing sequentially the manufacturing method of the eyeless suture needle.

First, the tabulation step S1-1 is performed in which a plate material is welded into a pipe-like shape. In this tabulation step S1-1, first, a coil-like stainless steel plate material (a metal plate material) 21 having a predetermined thickness is prepared. Then, as shown in FIG. 3A, by using a plurality of rolls 22, both end portions of the plate material 21 are butted to be a round pipe-like shape. Next, the abutting portion is welded by TIG welding or the like, and thereafter annealed, and cleaned to obtain a pipe element tube 23.

Figure 3B:
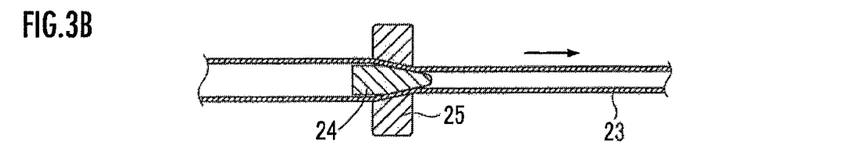

Next, as shown in FIG. 3B, core drawing step S1-2 is performed with respect to the obtained pipe element tube 23 in which the thickness is adjusted by using a cored bar (float) 24 and a dies 25. In the core drawing step S1-2, the inner and outer circumferential surface of the pipe element tube 23 is regulated to reduce the diameter by the cored bar 24 and the dies 25. In this core drawing step S1-2, the welding joint portion of the inner and outer circumferential surface of the pipe element tube 23 is eliminated and the thickness is determined.

Figure 3C:
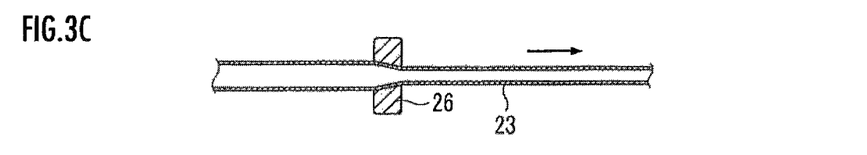

Then, as shown in FIG. 3C, the tube drawing step S1-3 is performed with respect to the pipe element tube 23 whose thickness is determined, by only using a dies 26 without the cored bar to adjust the outer form. In the tube drawing step S1-3, the outer circumferential surface of the pipe element tube 23 is regulated to reduce its diameter by the dies 26. In the tube drawing step S1-3, the outer diameter of the pipe element tube 23 is reduced to be a mirror-like surface. However, since the inner diameter is reduced in a state not being regulated, concavity and convexity are generated on the inner circumferential surface.

In the core drawing step S1-2 and the tube drawing step S1-3, annealing and cleaning is performed according to need, and the required inner and outer diameter is arranged. In the core drawing step S1-2 and the tube drawing step S1-3, if the diameter is largely reduced at one time, the pipe element tube 23 will rapture. Therefore, it is necessary to repeat the steps many times while annealing and cleaning.

In the core drawing step S1-2, no concavity and convexity are generated on the inner circumferential surface of the pipe element tube 23, and the concavity and convexity on the inner circumferential surface of the pipe element tube 23 become larger as the tube drawing step S1-3 is repeated. Therefore, by changing the repeating times of the core drawing step S1-2 and the tube drawing step S1-3, the surface roughness of the inner circumferential surface of the pipe element tube 23 varies. Accordingly, by arbitrarily setting each of the core reducing times by the core drawing step S1-2 and the tube drawing step S1-3, it is able to obtain the pipe element tube 23 having the concavity and convexity on the inner circumferential surface thereof with the surface roughness appropriate for the inner surface of the blind hole 6 of the eyeless suture needle 1.

Here, the tube drawing step S1-3 has better workability compared to the core drawing step S1-2 since the cored bar 24 is unnecessary. In order to make the surface roughness of the inner circumferential surface of the pipe element tube 23 fine, it is necessary to increase the number of times of the core drawing step S1-2 and lessen the amount of total diameter reduction by the tube drawing step S1-3, which is inferior in workability and increases the cost. On the other hand, in order to make the surface roughness of the inner circumferential surface of the pipe element tube 23 coarse, the number of times of the core drawing step S1-2 can be reduced and the amount of total diameter reduction by the tube drawing step S1-3 can be increased, thereby being superior in workability and decreases the cost. When the surface roughness of the inner circumferential surface of the pipe element tube 23 is from 5 μm to 15 μm, it belongs to the range with good workability and is also advantageous regarding cost.

By repeating the core drawing step S1-2 and the tube drawing step S1-3, and adjusting so as to obtain the predetermined inner diameter and the surface roughness of the inner circumferential surface between 5 μm and 15 μm at the end of the tube drawing step S1-3, the welded pipe element tube 23 having an uniform inner and outer diameter is obtained.

The pipe element tube 23 obtained as such is straightened and thereafter cut in an appropriate length to obtain the pipe 12 in the cutting step S1-4.

Figure 3D:
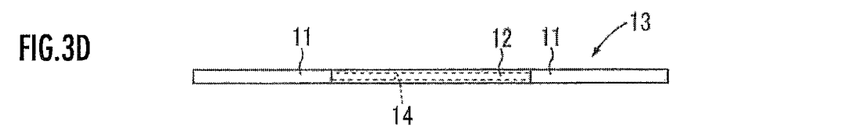

Next, as shown in FIG. 3D, step S2 is performed in which two linear materials 11 and the pipe 12 are joined by butt resistance welding to form a needle base material 13. In this step S2, while each of the linear material 11 and the pipe 12 is retained, by pressing from outer side, one end surface of each linear material 11 is butted to both end surfaces of the pipe 12 so that the outer circumferential surfaces thereof are flush.

Each of a vicinity of end surfaces of the linear material 11 and the pipe 12 which is abutted is retained by a pair of electrification electrodes which are not shown, and the electrification electrodes are electrified alternately. By doing so, the needle base material 13 in which a long blind hole 14 is formed in the central portion is obtained.

The joining can be performed by laser beam welding or electron beam welding. However, it is necessary to rotate or the like the linear material 11 when performing these welding. On the other hand, since butt resistance welding does not require rotating or the like of the linear material 11, a stable joining is possible, the process speed is fast, and the facility is simple. Therefore, it is most preferable to perform the joining of the linear material 11 and the pipe 12 by butt resistance welding.

Next, step S3 is performed, in which the joining portion is flushed by grinding or polishing a welding burr or a mount portion generated on the outer circumferential surface of the joining portion of the linear material 11 and the pipe 12 by the butt resistance welding. The outer circumferential surface of the joining surface is grinded and polished by using a pointed-end processing machine or a belt polishing machine or the like.

The needle base material 13 completed in such a way becomes the base material for manufacturing two eyeless suture needles 1 (refer to FIG. 1A). The blind hole 6 necessary for the thread attaching portion 2 is already provided by the pipe portion in this needle base material 13.

Figure 3E:
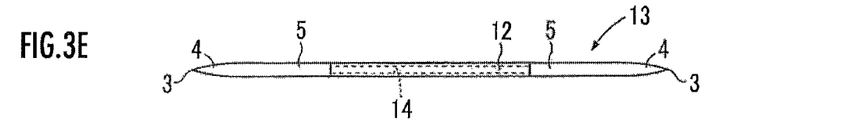

Next, as shown in FIG. 3E, step S4 is performed in which the linear material portion at both ends of the needle base material 13 is processed to form the needle tip portion 4 and the needle body portion 5. The needle tip portion 4 is formed as a triangular needle or a round needle by press process, or grinding and polishing process. In a case of a triangular needle, if it is able to make the burr thickness sufficiently thin at the time of triangular press process, the grinding and polishing process may be skipped and the cutting blade may be completed by electrolytic polishing step (S10) which will be explained later. The needle body portion 5 is press processed so that the cross section thereof becomes a triangle, a quadrangle, or a flat shape and the like.

In this step S4, the linear material 11 portion at both ends of the needle base material 13 can be processed while retaining the pipe portion of the needle base material 13. It is also able to perform step S3 and step S4 as a same step by incorporating the polishing of the joining portion into the step of processing the needle tip portion 4 to be a round needle.

Figure 3F:
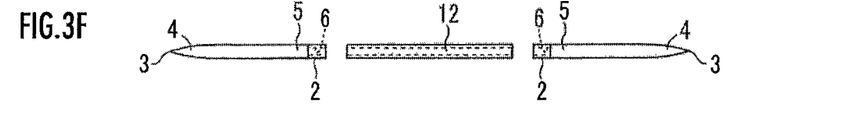

Next, as shown in FIG. 3F, step S5 is performed for cutting at predetermined positions so that a length for the thread attaching portion 2 is remained at each of both end portions of the pipe 12 by using a grindstone or the like. By making the cutting position to be a position for forming the blind hole 6 having an appropriate depth, it is able to provide a blind hole 6 with necessary and sufficient depth to the completed eyeless suture needle 1.

Next, step S6 for chamfer processing of the inner circumferential end portion of the thread attaching portion 2, is performed.

The pipe 12 is cut, and the opening portion of the blind hole 6 formed at the end surface of the pipe 12 is cut and grinded by two or more types of drills having mutually different point angles. By doing so, it is able to form the opening portion of the blind hole 6 to be substantially horn-like shape without any burrs.

Figure 4A:
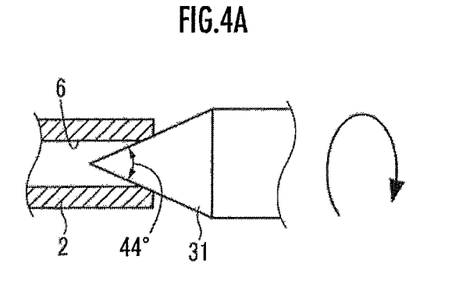
FIG. 4A to FIG. 4C are schematic views showing sequentially a chamfer process of an inner circumferential surface of an opening portion of a blind hole.
Figure 4B:
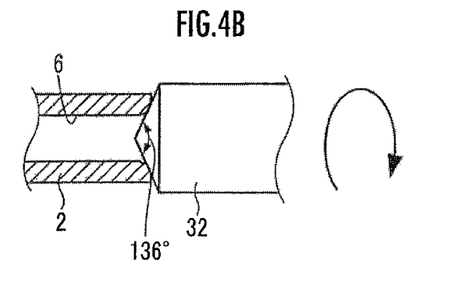
Figure 4C:
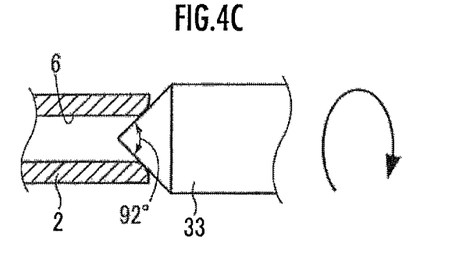

For example, as shown in FIG. 4A to FIG. 4C, the opening portion of the blind hole 6 is chamfered by using three types of different flat drills 31, 32, 33 with mutually different point angles. At this time, a first surface A1 is cut and grind processed by the flat drill 31 with a point angle 44 degrees, next, a third surface A3 is cut and grind processed by the flat drill 32 with a point angle 136 degrees, and lastly, a crossing portion of theses cut and grind processed surfaces is chamfer processed by the flat drill 33 with a point angle 92 degrees to provide a second surface A2.

Here, in a case chamfering is performed by using two types of different flat drills, for example, the first surface may be cut and grind processed by a flat drill with a point angle 60 degrees, and next, the second surface may be cut and grind processed by a flat drill with a point angle 120 degrees. In order to avoid the generation of burr at the time of chamfer process, it is preferable that a tip angle of each edge of the chamfer portion is 150 degrees or more.

By doing so, the cross section of the opening portion of the blind hole 6 becomes substantially horn-like shape. In the flat drills 31, 32, 33 used for this chamfer process, it is easy to manufacture the tip diameter to be approximately 10 μm. Moreover, even if the cutting blades of the flat drills 31, 32, 33 are worn, no burr is generated at the corner portion since cutting and grinding is performed in an order in which the angle of cutting intersections of each is 150 degrees or more.

Figure 3G:
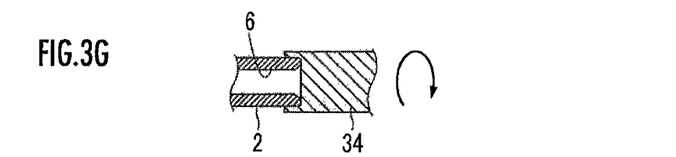

Next, as shown in FIG. 3G, step S7 for chamfer processing an outer circumference of the thread attaching portion 2 is performed. While rotating a tool 34 having a circular concavity substantially equal to the needle outer diameter, the tool 34 is pressed against the outer circumference of the end portion of the thread attaching portion 2. By doing so, the edge remaining at the outer circumference of the thread attaching portion 2 is rolled and eliminated. This outer periphery chamfer may be a chamfer of a degree so as not to be an obstacle when the eyeless suture needle 1 passes through a tissue of a human body.

Figure 3H:
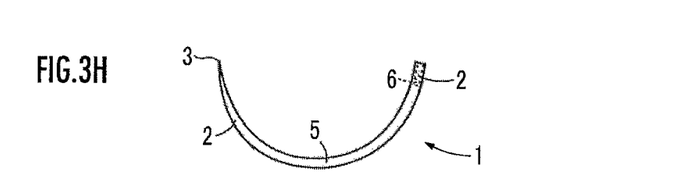

Next, as shown in FIG. 3H, step S8 for conducting bending process of the needle body portion 5 is performed. The needle body portion 5 is bent processed to be a substantially semicircular arc shape.

By using a grooved pulley in which a plurality of grooves for accommodating needle material are formed at the outer peripheral surface, conveyance, positioning, and processing can be automatically performed in succession in the above step 5 to step 8.

Next, step S9 for heat treatment of the needle tip portion 4 and the needle body portion 5 is performed.

Next, step S10 for polish finishing process of the needle tip portion 4, the needle body portion 5, and the pipe portion is performed.

Lastly, step S11 for providing chemical treatment using silicone and the like is performed.

By doing so, the eyeless suture needle 1 as shown in FIG. 1 can be obtained.

Figure 5:
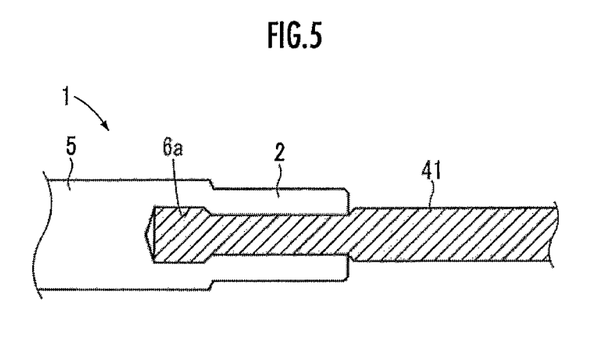
FIG. 5 is a schematic view showing a state in which a suture thread is caulked and fixed to the blind hole.

As explained above, the eyeless suture needle 1 manufactured by the manufacturing method of the embodiment of the present invention is able to keep all of the hole diameter error of the blind hole 6, the surface roughness of the inner surface of the blind hole 6, the shape of the opening portion of the blind hole 6, and the depth of the blind hole 6 within a permissible range which does not decrease the drawing strength of the suture thread 41 (refer to FIG. 5).

As shown in FIG. 5, the suture thread 41 is inserted to the blind hole 6 of such eyeless suture needle 1, and caulked and fixed, thereby enabling to achieve good workability, increase the quality of the completed suture needle with the needle, and equalization. Also reduction of cost can be attained by decreasing discarded needle due to attachment defect.

It is also acceptable to obtain one eyeless suture needle 1 from a needle base material in which the linear material 11 is joined to only one side of the pipe 12.

EXPLANATION OF THE REFERENCE NUMERALS

1 . . . eyeless suture needle, 2 . . . thread attaching portion, 3 . . . needle tip, 4 . . . needle tip portion, 5 . . . needle body portion, 6 . . . blind hole, 6a . . . inner circumferential surface of the blind hole, 11 . . . linear material (linear member), 12 . . . pipe (pipe-like member), 13 . . . needle base material, 14 . . . long blind hole, 21 . . . stainless steel plate material (metal plate material), 23 . . . pipe element tube, 24 . . . cored bar, 25 . . . dies, 26 . . . dies, 31, 32, 33 . . . flat drill (drill), 41 . . . suture thread

The invention claimed is:

1. A manufacturing method of an eyeless suture needle comprising;
    a step of obtaining a hollow cylindrical material by rolling a metal plate material, and welding abutting portions,
    a step of manufacturing a hollow cylindrical member including a core drawing step of reducing a diameter and adjusting a thickness of the hollow cylindrical material using a cored bar and a tube drawing step of reducing the diameter and adjusting an outer form of the hollow cylindrical material without using the cored bar, and by adjusting a number of times of repetition of the core drawing step and the tube drawing step, manufacturing the hollow cylindrical member having an annular shape cross section and having uniform concavity and convexity formed on an inner circumferential surface thereof, and
    a step of, while abutting linear members each having a circular shape cross section to end faces of the hollow cylindrical member, joining the linear members to the end faces of the hollow cylindrical member by butt resistance welding, and forming a joining portion in flush to obtain a needle base material which becomes a base material of two eyeless suture needles, and thereafter processing the linear members at each of both end portions of the needle base material to form needle tip portions, and thereafter cutting each of both end portions of the hollow cylindrical member of the needle base material with a length for thread attaching portions remaining on each of the linear portions.

2. The manufacturing method of the eyeless suture needle according to claim 1, wherein a surface roughness Rz of the inner circumferential surface of the hollow cylindrical member is 5 μm to 15 μm.

3. The manufacturing method of the eyeless suture needle according to claim 1, comprising a step of chamfer processing an opening portion of the hollow cylindrical member in a plurality of chamfer angles using a plurality of drills having different point angles.

* * * * *